United States Patent
Nöbel

(10) Patent No.: US 7,179,388 B2
(45) Date of Patent: Feb. 20, 2007

(54) METHOD FOR REMOVING FORMIC ACID FROM AQUEOUS SOLUTIONS

(75) Inventor: Thomas Nöbel, Maxdorf (DE)

(73) Assignee: BASF Aktiengesellschaft, Ludwigshafen (DE)

(*) Notice: Subject to any disclaimer, the term of this patent is extended or adjusted under 35 U.S.C. 154(b) by 355 days.

(21) Appl. No.: 10/473,203

(22) PCT Filed: Jun. 10, 2002

(86) PCT No.: PCT/EP02/06336

§ 371 (c)(1),
(2), (4) Date: Sep. 29, 2003

(87) PCT Pub. No.: WO02/100502

PCT Pub. Date: Dec. 19, 2002

(65) Prior Publication Data

US 2004/0094478 A1   May 20, 2004

(30) Foreign Application Priority Data

Jun. 11, 2001 (DE) ................................ 101 28 249

(51) Int. Cl.
*C02F 1/00* (2006.01)

(52) U.S. Cl. ............ 210/749; 210/758; 210/774; 568/864; 568/868; 203/28; 203/39

(58) Field of Classification Search ........... 210/634, 210/638, 749, 758, 760–763, 774; 568/376, 568/852–854, 864, 868; 549/266, 272; 203/28, 203/29, 36, 23
See application file for complete search history.

(56) References Cited

U.S. PATENT DOCUMENTS 2,938,924 A * 5/1960 Walter et al. ............... 568/358
3,597,330 A * 8/1971 Wegerich et al. ............. 203/29
4,110,372 A * 8/1978 Hey et al. .................... 562/606
5,370,801 A * 12/1994 Sorensen et al. ........... 210/742
5,981,769 A * 11/1999 Baur et al. .................. 549/266
6,008,418 A   12/1999 Baur et al.
6,734,326 B1 * 5/2004 Baud-Grasset et al. ..... 568/376

FOREIGN PATENT DOCUMENTS

SU         1933431          8/1983
WO     WO 01/32567    *   5/2001
WO        02/100502       12/2002

OTHER PUBLICATIONS

Hawley's Condensed Chemical Dictionary, 13th Edition, Revised by Richard Lewis, Copyright 1997.*
R.S.Coffey,Chemical Comm. 1967, 923-924.
Derwent Abst. 84-199128/19.
Derwent Abst. 89-303688/42—JP 1222-917-A.

* cited by examiner

Primary Examiner—Joseph Drodge
(74) Attorney, Agent, or Firm—Novak Druce & Quigg LLP

(57) ABSTRACT

Formic acid is at least partly removed from an aqueous solution comprising formic acid, cyclohexanone and cyclohexanol by decomposition over certain decomposition catalysts.

The method is preferably used for processing reaction products from the oxidation of cyclohexane and comprises:
(i) extracting a product gas mixture obtained in the oxidation of cyclohexane with an aqueous scrubbing liquid,
(ii) separating the aqueous solution obtained in (i) by distillation into an aqueous solution comprising formic acid, cyclohexanone and cyclohexanol together with further minor organic components and a carboxylic acid mixture
(iii) removing the formic acid at least partially from the aqueous solution obtained in (ii) by decomposition, and
(iv) further processing the aqueous solution obtained in (iii) to give epsilon-caprolactam, or using the aqueous solution obtained in (iii) as scrubbing liquid in (i).

2 Claims, No Drawings

METHOD FOR REMOVING FORMIC ACID FROM AQUEOUS SOLUTIONS

The present invention relates to a method of at least partly removing formic acid from an aqueous solution comprising formic acid, cyclohexanone and cyclohexanol as significant organic components.

Cyclohexanone and cyclohexanol, which are further processed to produce epsiloncaprolactam, are obtained industrially by oxidation of cyclohexane by means of oxygen or oxygen-containing gas. This gives a complex product mixture which comprises cyclohexanone and cyclohexanol as the main products of value together with 1,2- and 1,4-cyclohexanediol, adipic acid, 6-hydroxycaproic acid, glutaric acid, 5-hydroxyvaleric acid, formic acid and many further oxygen-containing components as by-products.

The abovementioned cyclohexanediols, monocarboxylic and dicarboxylic acids are separated off from the main products of value cyclohexane and cyclohexanol by extraction of this product mixture with an aqueous scrubbing liquid, giving an aqueous solution of the cyclohexanediols, monocarboxylic and dicarboxylic acids and further organic components. In addition, this contains small amounts of the desired products cyclohexanone and cyclohexanol. The aqueous solution, known as dicarboxylic acid solution, is subsequently dewatered by distillation in a column to give an aqueous stream comprising formic acid, cyclohexanone and cyclohexanol as significant organic components at the top of the column.

1,6-hexanediol is obtained from the dewatered carboxylic acid mixture by esterification, hydrogenation and distillation. The aqueous product taken off the top of the column, which comprises formic acid, cyclohexanone and cyclohexanol, has hitherto been discarded, for example passed to a water treatment plant or burnt. Further utilization of the aqueous solution comprising cyclohexanone, cyclohexanol and formic acid, for example by separating off cyclohexanone and cyclohexanol and processing them further to give epsilon-caprolactam, has hitherto been nonviable as a result of the corrosion problems caused by formic acid.

It is known from R. S. Coffey, Chemical Communications, 1967, pp. 923–24, that formic acid can be decomposed over phosphine complexes of the noble metals Rh, Ru, Ir and Pt to form $CO_2$ and $H_2$.

SU-A 1 033 431 describes the decomposition of formic acid into CO and $H_2O$ over a catalyst comprising CaO and $P_2O_5$ or CaO, $P_2O_5$ and $B_2O_3$.

JP-A 1222917 describes the decomposition of formic acid over oxides and hydroxides of zirconium, titanium, aluminum and iron which have been treated with a sulfate solution and subsequently calcined.

It is an object of the present invention to provide a simple and inexpensive method of working up the aqueous solutions comprising cyclohexane, cyclohexanol and formic acid which are obtained in the dewatering by distillation of carboxylic acid solutions obtained in the water extraction of the product mixture from the oxidation of cyclohexane and passing them to a further use.

We have found that this object is achieved by a method of at least partly removing formic acid from an aqueous solution comprising formic acid, cyclohexanone and cyclohexanol, which comprises decomposing the formic acid over a basic metal oxide of metals of groups 2, 4, 5, 12 and/or 14 or over a noble metal of groups 8–11 on an oxidic or nonoxidic support as decomposition catalyst.

The formic acid is decomposed over the decomposition catalysts to form gaseous decomposition products, predominantly $CO_2$ and $H_2$.

The method of the present invention makes it possible to remove formic acids selectively from the aqueous solutions without degradation of the components cyclohexanone and cyclohexanol present as desired products occurring at the same time. It is surprising that neither a loss of cyclohexanone as a result of base-catalyzed aldol condensation of cyclohexanone nor a loss of cyclohexanol as a result of elimination to form cyclohexene occurs under the reaction conditions.

Suitable basic metal oxides of metals of groups 2, 4, 5, 12 and 14 are BeO, MgO, CaO, BaO, $TiO_2$, $ZrO_2$, $V_2O_5$, ZnO, CdO and $SnO_2$. Suitable metals of groups 8–11 are Ru, Rh, Ir, Ni, Pd, Pt, Cu, Ag and Au. Suitable oxidic supports are, for example, $Al_2O_3$, $TiO_2$, MgO, while a suitable nonoxidic support is activated carbon (C).

Preferred decomposition catalysts are ZnO and mixtures of ZnO and CaO, and an abovementioned noble metal on activated carbon.

The decomposition is usually carried out at from 100 to 400° C., preferably from 150 to 350° C., particularly preferably from 170 to 220° C. The residence time is, for example, from 1 to 6 hours. In general, at least 90%, preferably at least 95%, particularly preferably at least 98%, of the formic acid is decomposed.

The decomposition can be carried out batchwise or continuously over a suspended or fixed-bed catalyst, for example in the upflow or downflow mode. The decomposition is preferably carried out continuously, particularly preferably over a fixed-bed decomposition catalyst. Examples of suitable reactors are tube reactors containing a fixed catalyst bed.

The aqueous solution comprising formic acid, cyclohexanone and cyclohexanol is usually obtained by extraction of the gas mixture obtained in the oxidation of cyclohexane by means of oxygen or an oxygen-containing gas using an aqueous scrubbing liquid and distillation of the resulting aqueous solution comprising carboxylic acids.

The aqueous solution obtained in this way, from which the formic acid is at least partly removed by the method of the present invention, generally comprises (a) from 3 to 6% by weight of formic acid,
(b) from 0.1 to 2% by weight of cyclohexanol,
(c) from 0.1 to 2% by weight of cyclohexanone,
(d) from 92 to 96.8% by weight of water.

The present invention also provides a process for the further processing of reaction products of the oxidation of cyclohexane, which comprises the steps (i) extraction of the product gas mixture obtained in the oxidation of cyclohexane using an aqueous scrubbing liquid to give an aqueous solution comprising carboxylic acids, (ii) separation of the aqueous solution comprising carboxylic acids obtained in step (i) into an aqueous solution comprising formic acid, cyclohexanone and cyclohexanol together with further minor organic components and a carboxylic acid mixture by distillation, with the carboxylic acid mixture being able to be processed further in a customary manner to give 1,6-hexanediol, (iii) at least a partial removal of the formic acid from the aqueous solution comprising formic acid, cyclohexanone and cyclohexanol obtained in step (ii) by decomposition of the formic acid over a basic metal oxide of metals of groups 2, 4, 5, 12 and/or 14 or over a noble metal of groups 8–11 on an oxidic or nonoxidic support as decomposition catalyst, (iv) further processing of the aqueous solution comprising cyclohexanone and cyclohexanol obtained in step (iii) to give epsilon-caprolactam, or use of the aqueous solution comprising cyclohexanone and cyclohexanol obtained in step (iii) as scrubbing liquid in step (i).

In step (i), the product mixture obtained in the oxidation of cyclohexane is extracted with an aqueous scrubbing liquid to give an aqueous solution comprising carboxylic acids. This aqueous solution usually comprises from 10 to 40% by weight of adipic acid, from 10 to 40% by weight of 6-hydroxycaproic acid, from 1 to 10% by weight of glutaric acid, from 1 to 10% by weight of 5-hydroxyvaleric acid, from 1 to 5% by weight of 1,2-cyclohexanediol, from 1 to 5% by weight of 1,4-cyclohexanediol, from 2 to 10% by weight of formic acid, from 0.1 to 2% by weight of cyclohexanone, from 0.1 to 2% by weight of cyclohexanol together with many further monocarboxylic and dicarboxylic acids, esters, oxo compounds and oxa compounds whose individual contents generally do not exceed 5% by weight, e.g. acetic acid, propionic acid, butyric acid, valeric acid, caproic acid, oxalic acid, malonic acid, succinic acid, 4-hydroxybutyric acid and gamma-butyrolactone.

In step (ii), the aqueous solution comprising formic acid, cyclohexanone and cyclohexanol is separated off by distillation. The carboxylic acid mixture which remains can be processed in a customary manner to give 1,6-hexanediol, for example as described in WO 97/31882. For this purpose, the monocarboxylic and dicarboxylic acids present in the carboxylic acid mixture are reacted with a low molecular weight alcohol to form the corresponding carboxylic esters, the esterification mixture obtained is freed of excess alcohol and low boilers in a first distillation step, the bottom product is freed of cyclohexanediols in a further distillation step, the ester fraction is catalytically hydrogenated and 1,6-hexanediol is isolated from the product mixture from the hydrogenation by distillation.

The cyclohexanone- and cyclohexanol-containing aqueous solution obtained in step (iii), which has been depleted in formic acid, can be processed further to give epsilon-caprolactam. Such further processing is not possible without prior removal of formic acid because of the corrosion problems caused by the latter. In this further processing, cyclohexanone and cyclohexanol are separated off from the aqueous solution by distillation, cyclohexanol is oxidized to cyclohexanone and epsilon-caprolactam is prepared from the cyclohexanone in a manner known per se.

The aqueous solution which has been depleted in formic acid can also be used as scrubbing liquid in step (i). In this way, the losses of cyclohexanone and cyclohexanol caused by the extraction step (i) are minimized.

Alternatively, the aqueous solution which has been depleted in formic acid can be passed as wastewater to a water treatment plant. Here, the reduced TOC content of the wastewater is advantageous.

The invention is illustrated by the following example.

EXAMPLE 32.1 g of the aqueous solution comprising formic acid, which has been obtained by dewatering by distillation of the aqueous solution comprising carboxylic acids obtained by extraction of the product gases from the oxidation of cyclohexane with water, are placed in a 50 ml autoclave. This aqueous solution comprising formic acid had the following composition:
6% by weight of formic acid,
1% by weight of cyclohexanone,
1% by weight of cyclohexanol,
92% by weight of water.

The mixture is admixed with 10 g of the decomposition catalyst indicated in the table below in powder form or in the form of granules. The mixture is heated to 170–200° C. over a period of from 2 to 4 hours, with an increasing pressure being observed as a result of the gaseous decomposition products (CO, $CO_2$ and $H_2$). After cooling the reaction mixture, the formic acid content is determined by acid/base titration. The cyclohexanone and cyclohexanol contents were determined by gas chromatography and remained unchanged.

| Acid number/pH (beforehand) | Temperature [° C.] | Residence time [h] | Pressure[1] [bar] | Acid number/pH (afterwards) |
|---|---|---|---|---|
| Catalyst: ZnO as extrudates | | | | |
| 75/1.0 | 170 | 2 | 15 | 42/6.0 |
| 75/1.1 | 170 | 4 | 25 | 29/6.0 |
| 75/1.1 | 190 | 2 | 25 | 17/6.1 |
| 75/1.2 | 190 | 4 | 55 | <1/6.6 |
| 88/1.1 | 200 | 2 | 80 | 5.3/6.5 |
| 88/1.0 | 200 | 4 | 70 | 1.4/4.7 |
| 75/1.2 | 210 | 2 | 70 | 2/6.3 |
| 88/1.0 | 220 | 2 | 70 | <0.5/7.0 |
| 88/1.1 | 220 | 4 | 70 | <0.5/6.9 |
| Catalyst: 50% by weight of ZnO/50% by weight of CaO/calcite as shaped bodies | | | | |
| 78/1.1 | 190 | 2 | 55 | 1.5/6.2 |
| 78/1.1 | 200 | 2 | 57 | 2.4/6.4 |
| 78.1/1.1 | 210 | 2 | 68 | 0.9/6.2 |
| Catalyst: 50% by weight of ZnO/50% by weight of CaO as shaped bodies | | | | |
| 78/1.1 | 200 | 2 | 50 | <0.5/5.8 |
| 78/1.1 | 190 | 2 | 62 | 1.2/5.9 |

[1]measured final pressure

I claim:

1. A method of selectively at least partly removing formic acid from an aqueous solution comprising formic acid, cyclohexanone and cyclohexanol, with the amount of formic acid being equal to or higher than the amount of the cyclohexanone or the amount of the cyclohexanol and the amount of the formic acid being at least 2% by weight, which comprises decomposing the formic acid over a basic metal oxide of metals of groups 2, 4, 5, 12 and/or 14 or over a noble metal of groups 8–11 at a concentration sufficient for chemical decomposition of the formic acid wherein the aqueous solution comprising formic acid, cyclohexanone and cyclohexanol is obtained by extraction of the product gas mixture obtained in the oxidation of cyclohexane by means of oxygen or an oxygen-containing gas using an aqueous scrubbing liquid and distiallation of the resulting aqueous carboxylic acid solution.

2. A process for the further processing of reaction products of the oxidation of cyclohexane, which comprises the steps of:
(i) extraction of the product gas mixture obtained in the oxidation of cyclohexane using an aqueous scrubbing liquid to give an aqueous solution comprising carboxylic acids, (ii) separation of the aqueous solution comprising carboxylic acids obtained in step (i) into an aqueous solution comprising formic acid, cyclohexanone and cyclohexanol together with further minor organic components and a carboxylic acid mixture by distillation, (iii) selectively at least partially removing the formic acid from the aqueous solution comprising formic acid, cyclohexanone and cyclohexanol obtained in step (ii) by decomposition of the formic acid over a basic metal oxide of metal groups 2, 4, 5, 12 and/or 14 or over a noble metal of groups 8–11 on an oxidic or nonoxidic support as decomposition catalyst, (iv) further processing of the aqueous solution comprising cyclohexanone and cyclohexanol obtained in step (iii) to give epsilon-caprolactam, or use of the aqueous solution comprising cyclohexanone and cyclohexanol obtained in step (iii) as scrubbing liquid in step (i).

\* \* \* \* \*